US011890345B2

(12) United States Patent
Di Stefano

(10) Patent No.: US 11,890,345 B2
(45) Date of Patent: Feb. 6, 2024

(54) COMPOSITIONS COMPRISING VITAMINS/MINERALS IN A POLYPHENOLIC MATRIX, METHODS AND USES THEREOF

(71) Applicant: ProMedX Innovations Inc., Thornhill (CA)

(72) Inventor: Fabrizio Di Stefano, Bolton (CA)

(73) Assignee: ProMedXInnovations Inc., Thornhill (CA)

( * ) Notice: Subject to any disclaimer, the term of this patent is extended or adjusted under 35 U.S.C. 154(b) by 0 days.

(21) Appl. No.: 17/517,197

(22) Filed: Nov. 2, 2021

(65) Prior Publication Data
US 2022/0143192 A1 May 12, 2022

Related U.S. Application Data

(60) Provisional application No. 63/110,495, filed on Nov. 6, 2020.

(51) Int. Cl.
| | |
|---|---|
| *A61K 47/46* | (2006.01) |
| *A61K 45/06* | (2006.01) |
| *A61K 47/38* | (2006.01) |
| A61K 31/375 | (2006.01) |
| A61K 36/185 | (2006.01) |
| A61K 36/73 | (2006.01) |
| A61K 47/36 | (2006.01) |
| A61P 3/02 | (2006.01) |
| A61K 9/107 | (2006.01) |

(52) U.S. Cl.
CPC .............. *A61K 47/46* (2013.01); *A61K 45/06* (2013.01); *A61K 47/38* (2013.01)

(58) Field of Classification Search
CPC ........ A61K 47/46; A61K 45/06; A61K 47/38; A61K 31/375; A61K 36/185; A61K 36/73; A61K 47/36; A61K 9/107; A61P 3/02
See application file for complete search history.

(56) References Cited

U.S. PATENT DOCUMENTS

| | | | |
|---|---|---|---|
| 8,168,225 B2 | 5/2012 | Giner et al. | |
| 2004/0156873 A1 | 8/2004 | Gupta | |
| 2006/0035981 A1 | 2/2006 | Mazzio et al. | |

FOREIGN PATENT DOCUMENTS

| | | | | |
|---|---|---|---|---|
| JP | 2007143413 | * | 2/2007 | ............ A23L 1/015 |
| WO | 0056346 A1 | | 9/2000 | |
| WO | 2013054304 A1 | | 4/2013 | |
| WO | WO-2013054304 A1 | * | 4/2013 | .......... A61K 31/352 |
| WO | 2014074765 A2 | | 5/2014 | |

OTHER PUBLICATIONS

Aguilera, Critical Reviews in Food Science and Nutrition, 2019, vol. 59, No. 22, 3612-3629 (Year: 2019).*
Karan. Handbook of Pharmaceutical Wet Granulation, 2019 (Year: 2019).*
Sun et al. Journal of Integrative Agriculture, 2017, 18(8): 1808-1818, herein after Sun (Year: 2017).*
Kenyon. Encapsulation and Controlled Release of Food Ingredients, chap. 4, p. 42-50, 1995 (Year: 1995).*
Manseau, Dannielle, "PCT International Search Report and Written Opinion," PCT Application No. PCT/CA2021/051555, dated Jan. 4, 2022, 12 pages.
Gullon, Patricia et al., "Pomegranate Peel as Suitable Source of High-Added Value Bioactives: Tailored Functionalized Meat Products," Molecules (2020) 25, 2859; doi:10.3390/molecules25122859, www.mdpi.com/journal/molecules, 18 pages.
Zheng, L. et al, "Microencapsulation of bayberry polyphenols by ethyl cellulose: Preparation and characterization," Journal of Food and Engineering 104 (2011) 89-95, 7 pages.
Sosa, M. V., et al, "Green tea encapsulation by means of high pressure antisolvent coprecipitation", The Journal of Supercrit Fluids, 56 (2011) 304-311, 8 pages.
Flores, F. P., et al., "Physical and storage properties of spray-dried blueberry pomace extract with whey protein isolate as wall material," Journal of Food Engineering, 137 (2014) 1-6, 6 pages.
Lupo, B., et al, "Preparation of alginate microspheres by emulsification/internal gelation to encapsulate cocoa polyphenols," Food Hydrocolloid 38 (2014) 56-65, 10 pages.
Visentin, A., et al., "Precipitation and encapsulation of rosemary antioxidants by supercritical antisolvent process," Journal of Food Engineering109 (2012) 9-15, 7 pages.

* cited by examiner

*Primary Examiner* — Mark L Shibuya
*Assistant Examiner* — Luisalberto Gonzalez
(74) *Attorney, Agent, or Firm* — BERESKIN & PARR LLP/S.E.N.C.R.L., s.r.l.

(57) ABSTRACT

The present application relates to compositions comprising vitamins and/or minerals and a polyphenolic matrix having increased stability and bioavailability. The polyphenolic matrix may comprise a polyphenolic extract, an emulsifier and a binder. The polyphenolic extract may be a fruit peel extract. The present application further relates to uses and methods using the compositions of the application.

20 Claims, No Drawings

COMPOSITIONS COMPRISING VITAMINS/MINERALS IN A POLYPHENOLIC MATRIX, METHODS AND USES THEREOF

CROSS-REFERENCE TO RELATED APPLICATIONS

This application claims benefit of U.S. Provisional Application No. 63/110,495 filed on Nov. 6, 2020, which is incorporated by reference herein in its entirety.

FIELD

The present application relates generally to formulations comprising vitamins and/or minerals, and more specifically to formulations comprising vitamins and/or minerals in a polyphenolic matrix, preparations and uses thereof.

BACKGROUND

Vitamins and minerals are essential micronutrient required by organisms for proper functioning of their metabolism. These essential nutrients cannot be synthesized in the organism, either at all or not in sufficient quantities, and therefore must be obtained through the diet. Vitamins have diverse biochemical functions. For example, Vitamin A acts as a regulator of cell and tissue growth and differentiation. Vitamin D provides a hormone-like function, regulating mineral metabolism for bones and other organs. The B complex vitamins function as enzyme cofactors (coenzymes) or the precursors for them. Vitamins C and E function as antioxidants. Both deficient and excess intake of a vitamin can potentially cause clinically significant illness.

Vitamin/mineral deficiency may be due to improper or inadequate diet (primary deficiency) or may be caused by an underlying disorder (secondary deficiency), including a variety of diseases or conditions. Examples are diseases of the liver and biliary tract, prolonged diarrheas from any cause, hyperthyroidism, anemia together with a variety of other disorders of the digestive system, including those related to alcoholism. There are numerous available vitamin supplements, in the form of tablets, capsules and injections, to aid in the treatment of such vitamin deficiencies. The effectiveness of the intake of such vitamin compositions is dependent upon the level of bioavailability of these vitamins in the patient's system.

Bioavailability refers to how much, and at what rate, an active substance gets absorbed by bloodstream. It's important to understand the bioavailability of a substance because it helps determine how much a user needs to consume—and in what form—to ensure a proper dose actually enters their system. Otherwise, the desired effects may not be provided. Various physiological factors reduce the availability of drugs prior to their entry into the systemic circulation, the formulation being one important factor. Bioavailability may be expressed in average percentage over a predetermined time versus concentration of drug substance or vitamin in blood plasma.

Bioavailability of vitamins is tightly bound to their stability. A number of common physical and chemical factors affect the stability of vitamins such as light, heat, moisture, oxygen, and pH, and contact with other compounds. Exposure to multiple stresses generally multiplies the effect on vitamin stability. These factors subject vitamins to degradation primarily through oxidation. Strategies for improving vitamin stability through product formulation have been developed, for examples by using metabolites, different formulation methods and conditions. However, many formulations still present poor stability and bioavailability.

In view of the above, there is a need for formulations which show enhanced bioavailability, biological stability, and consistent delivery of vitamins and minerals.

SUMMARY

It is an object of the present application to provide formulations comprising vitamins or minerals which show good bioavailability, biological stability, and consistent delivery.

It has been surprisingly shown herein that compositions comprising vitamins or minerals formulated within polyphenolic matrix provide good stability and bioavailability highlighting the surprising results obtained with the compositions of the application.

Accordingly, the present application includes a composition comprising at least one vitamin and mineral, and a polyphenolic matrix.

The present application further includes a composition comprising at least one vitamin and mineral in a polyphenolic matrix comprising a mixture of at least one polyphenolic extract, at least one emulsifier and at least one binder.

The present application also includes a composition comprising at least one vitamin and mineral in a polyphenolic matrix comprising a mixture of at least one fruit peel extract, at least one emulsifier and at least one binder.

The present application further includes a composition comprising at least one vitamin and mineral in a polyphenolic matrix comprising a mixture of at least one pomegranate peel extract, at least one *Quillaja saponaria* extract and at least one modified food starch.

The present application further provides a method for preventing or treating vitamin or mineral deficiency, said method comprising administering a therapeutically effective amount of a composition of the present application a subject in need thereof.

The present application further includes a method for producing a composition comprising at least one vitamin and mineral, and a polyphenolic matrix, the method comprising: mixing said at least one vitamin and mineral, and said polyphenolic matrix; homogenizing the mixture to allow encapsulation of at least one vitamin and mineral in the polyphenolic matrix.

The present application also provides a method for producing a composition comprising at least one vitamin and mineral in a polyphenolic matrix comprising a mixture of at least one polyphenolic extract, at least one emulsifier and at least one binder, the method comprising: mixing said at least one polyphenolic extract, said at least one emulsifier and said at least one binder to provide a pre-complexing mixture; mixing said at least one vitamin and mineral with the pre-complexing mixture; homogenizing the mixture obtained in b) to allow encapsulation of at said least one vitamin and mineral in the polyphenolic matrix.

The present application further includes a method for producing a composition comprising at least one vitamin and mineral in a polyphenolic matrix comprising a mixture of at least one fruit peel extract, at least one emulsifier and at least one binder, the method comprising: mixing at least one polyphenolic extract, said at least one emulsifier and said at least one binder, wherein said at least one emulsifier is selected from the group consisting of *Quillaja saponaria* extract, locust bean gum, gum arabic, cellulose gum, xanthan gum and combinations thereof and said at least one binder is selected from the group consisting of modified food starch, maltodextrin, cyclodextrin, gum arabic, inulin, and combinations thereof, to provide a pre-complexing mixture; mixing said at least one vitamin and mineral with the pre-complexing mixture; homogenizing the mixture obtained in b) to allow encapsulation of at said least one vitamin and mineral in the polyphenolic matrix.

The present application provides a composition obtained by a method of the present application.

The present application includes use of the composition of the present application for the manufacture of a vitamin and/or mineral supplement.

The present application also provides use of the composition of the present application, for preventing or treating vitamin and/or mineral deficiency.

Other features and advantages of the present application will become apparent from the following detailed description. It should be understood, however, that the detailed description and the specific examples, while indicating embodiments of the application, are given by way of illustration only and the scope of the claims should not be limited by these embodiments, but should be given the broadest interpretation consistent with the description as a whole.

DETAILED DESCRIPTION

I. Definitions

Unless otherwise indicated, the definitions and embodiments described in this and other sections are intended to be applicable to all embodiments and aspects of the present application herein described for which they are suitable as would be understood by a person skilled in the art.

The term "composition(s) of the application" or "composition(s) of the present application" and the like as used herein refers to a composition, such a pharmaceutical composition, comprising combinations of compounds, as described in the application, and may further contain any acceptable carrier.

The term "and/or" as used herein means that the listed items are present, or used, individually or in combination. In effect, this term means that "at least one of" or "one or more" of the listed items is used or present.

As used in the present application, the singular forms "a", "an" and "the" include plural references unless the content clearly dictates otherwise. For example, an embodiment including "a composition" should be understood to present certain aspects with one compound, or two or more additional compounds.

As used in this application and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

The term "consisting" and its derivatives as used herein are intended to be closed terms that specify the presence of the stated features, elements, components, groups, integers, and/or steps, and also exclude the presence of other unstated features, elements, components, groups, integers and/or steps.

The term "consisting essentially of", as used herein, is intended to specify the presence of the stated features, elements, components, groups, integers, and/or steps as well as those that do not materially affect the basic and novel characteristic(s) of these features, elements, components, groups, integers, and/or steps.

The term "suitable" as used herein means that the selection of the particular compound or conditions would depend on the specific manipulation to be performed, the identity of the compound to be transformed and/or the specific use for the compound, but the selection would be well within the skill of a person trained in the art.

The present description refers to a number of chemical terms and abbreviations used by those skilled in the art.

The terms "about", "substantially" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies or unless the context suggests otherwise to a person skilled in the art.

The term "subject" as used herein includes all members of the animal kingdom including mammals, and suitably refers to humans. Thus the methods and uses of the present application are applicable to both human therapy and veterinary applications.

The term "pharmaceutically acceptable" means compatible with the treatment of subjects.

The term "pharmaceutically acceptable carrier" means a non-toxic solvent, dispersant, excipient, adjuvant or other material which is mixed with the active ingredient in order to permit the formation of a pharmaceutical composition, i.e., a dosage form capable of administration to a subject.

The term "treating" or "treatment" as used herein and as is well understood in the art, means an approach for obtaining beneficial or desired results, including clinical results. Beneficial or desired clinical results include, but are not limited to alleviation or amelioration of one or more symptoms or conditions, diminishment of extent of disease, stabilized (i.e. not worsening) state of disease, preventing spread of disease, delay or slowing of disease progression, amelioration or palliation of the disease state, diminishment of the reoccurrence of disease, and remission (whether partial or total), whether detectable or undetectable. Treatment methods comprise administering to a subject a therapeutically effective amount of one or more of the compositions of the application and optionally consist of a single administration, or alternatively comprise a series of administrations.

"Palliating" a disease, disorder or condition means that the extent and/or undesirable clinical manifestations of a disease, disorder or condition are lessened and/or time course of the progression is slowed or lengthened, as compared to not treating the disorder.

The term "prevention" or "prophylaxis", or synonym thereto, as used herein refers to a reduction in the risk or probability of a patient becoming afflicted with a disease, disorder or condition or manifesting a symptom associated with a disease, disorder or condition.

As used herein, the term "effective amount" or "therapeutically effective amount" means an amount of one or more compositions of the application that is effective, at dosages and for periods of time necessary to achieve the desired result.

The term "administered" as used herein means administration of a therapeutically effective amount of one or more compositions of the application to a subject.

The term "vitamin" as used herein refers to an organic molecule, or a set of molecules closely related chemically, that is an essential micronutrient which an organism needs in small quantities for the proper functioning of its metabolism. Most vitamins are not single molecules, but groups of related molecules called vitamers. For example, vitamin E consists of four tocopherols and four tocotrienols. Vitamins are classified as oil-soluble vitamins and water soluble vitamins and both are generally intended by the term "vitamin" used herein. Specifically, major health organizations list thirteen: vitamin A (as all-trans-retinol, all-trans-retinylesters, as well as all-trans-beta-carotene and other provitamin A carotenoids), vitamin B1 (thiamine), vitamin B2 (riboflavin), vitamin B3 (niacin), vitamin B5 (pantothenic acid), vitamin B6 (pyridoxine), vitamin B7 (biotin), vitamin B9 (folic acid or folate), vitamin B12 (cobalamins), vitamin C (ascorbic acid), vitamin D (calciferols), vitamin E (tocopherols and tocotrienols), and vitamin K (phylloquinone and menaquinones).

The term "mineral" as used herein refers to a chemical element required as an essential nutrient by organisms to perform functions necessary for life. For example, the five major mineral nutrients in the human body are calcium, phosphorus, potassium, sodium, and magnesium, but minerals also include remaining elements in a human body, being called "trace elements", that have a specific biochemical function such as sulfur, iron, chlorine, cobalt, copper, zinc, manganese, molybdenum, iodine, and selenium.

The term "deficiency" as used herein, when referring to vitamin deficiency, refers to the condition of a lack of a vitamin, caused by not enough vitamin intake which is defined as a primary deficiency, or due to an underlying disorder such as malabsorption which is called a secondary deficiency. Used herein, deficiency generally refers to both types of deficiencies.

The term "extract" is the result of a separation or isolation process of substances from a matrix or raw material. For example, extracts are obtained from the separation of certain desired components from the whole or part of a plant, such as its leaves, flowers, fruits, peel, bark, etc.

The term "bioavailability" as used herein refers to the proportion of a drug or other substance which enters the circulation (bloodstream) when introduced into the body and so is able to have an active effect.

The terms "polyphenolic" or "polyphenols" as used herein refer to naturally occurring organic compounds characterized by multiple phenol units, abundantly found in plants. Polyphenols include phenolic acids, flavonoids, stilbenes, and lignans.

The term "matrix" as used herein refers to a material comprising at least one or a mixture of specific molecules, intended for encapsulation or protection.

The term "matrix encapsulation" as used herein refers to a matrix forming a protective chemical structure for surrounding a bioactive compound.

II. Compositions of the Application

It has been surprisingly shown herein that compositions comprising vitamins and/or minerals formulated within a polyphenolic matrix provide good stability and bioavailability, highlighting the surprising results obtained with the compositions of the application.

Accordingly, the present application includes compositions comprising at least one vitamin and mineral and a polyphenolic matrix.

In some embodiments, the compositions of the present application may further comprise a pharmaceutically acceptable carrier. It is to be understand that any suitable pharmaceutically acceptable carrier know in the art may be used.

In some embodiments, a composition of the application is orally administered, for example, including an inert diluent or an assimilable edible carrier, or it is enclosed in hard or soft shell gelatin capsules, or it is compressed into tablets, or it is incorporated directly with the food of the diet. In some embodiments, the compound is incorporated with excipient and used in the form of ingestible tablets, buccal tablets, troches, capsules, caplets, pellets, granules, lozenges, chewing gum, powders, syrups, elixirs, wafers, aqueous solutions and suspensions, and the like.

In some embodiments, liquid preparations for oral administration take the form of, for example, solutions, syrups or suspensions, or they are suitably presented as a dry product for constitution with water or other suitable vehicle before use. When aqueous suspensions and/or emulsions are administered orally, the composition of the application is suitably suspended or dissolved in an oily phase that is combined with emulsifying and/or suspending agents. If desired, certain sweetening and/or flavoring and/or coloring agents are added. Such liquid preparations for oral administration are prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbic acid). Useful diluents include lactose and high molecular weight polyethylene glycols.

In some embodiments, the pharmaceutically acceptable carrier is a polyphenolic matrix comprising at least one polyphenolic extract, at least one emulsifier and at least one binder. For example, the polyphenolic extract is selected from the group consisting of a fruit peel extract, gallic acid, ellagic acid, punicalagin, catechin, chlorogenic acid, epicatechin and combinations thereof. In some embodiments, the fruit peel extract is selected from the group consisting of pomegranate peel extract, banana peel extract, amla peel extract, orange peel extract, mango peel extract, melon peel extract, water melon peel extract, tea extract and combinations thereof. In some embodiment, the fruit peel extract is pomegranate peel extract. It will be understood that polyphenolic extract may be obtained from any suitable extraction process know in the art and this is well within the purview of a skilled person.

Polyphenols are large family of compounds present in plants which are involved in the defense mechanism of the plant against UV radiation or pathogenic invasions. They are generally classified on the basis of number of phenol rings that they contain or the structural elements that bind these rings to one another. Polyphenolic compounds are known to have antioxidant, antimicrobial, anti-inflammatory and other health-promoting characteristics. These polyphenols actively work against reactive oxygen species generated by exogenous chemicals or endogenous metabolism and protects from damage caused by oxidative stress. The antioxidant properties of polyphenols make them interesting candidates for vitamins/minerals formulations.

From the library of natural polyphenols, pomegranate peel polyphenols received considerable attention due to the presence of diverse, bioactive polyphenols. Pomegranate, botanically known as *Punica granatum*, is an edible fruit enriched with therapeutically significant phytochemicals, predominantly present in the fruit peel. Pomegranates are rich sources of many phenolic compounds including ellagitannins (punicalagin, punicalin, pedunculagin, gallagic acid, ellagic acid, ellagitannin and gallotannins, anthocyanins (cyanidin delphinidin and pelargonidin glycosides), flavonoids (quercetin, kaempferol and luteolin glycosides, phlorodizin, rutin) and phenolic acids (caffeic acid, chlorogenic acid, o-coumaric acid, p-coumaric acid, ferulic acid, syringic acid, vanillic acid). Punicalagin is the polyphenol with the highest molecular weight and most abundant known to date in pomegranates. The phenol punicalagin is responsible for more than half of the juice's potent antioxidant activity. The presence of 16 hydroxyl group attached to the molecules is suspected to provide for the exceptional antioxidant activity of punicalagin. Pomegranate peel is a good source of bioactive compounds, including phenolic acids, flavonoids and hydrolyzable tannins, which are believed to have beneficial health effects, as previously discussed. The pomegranate's arils contain a substantial amount of polyphenols such as gallic acid, procatechuic acid, chlorogenic acid, caffeic acid, ferulic acid, coumaric acid and catechin. Polyphenols are consumed daily in the human diet and are associated with reduced risk of a number of chronic diseases, including cancer, cardiovascular disease, and diabetes. The health benefits of polyphenols have been attributed to their antioxidant activity, but many studies might be hampered by oral administration and poor bioavailability. In view of the above, a polyphenol matrix made from pomegranate peel extract may prove beneficial in the formulation of vitamins and minerals.

In some embodiments, the emulsifier is selected from the group consisting of *Quillaja saponaria* extract, locust bean gum, gum arabic, cellulose gum, xanthan gum and combinations thereof. In some embodiments, the emulsifier is *Quillaja saponaria* extract.

*Quillaja saponaria* extract is typically obtained by aqueous extraction of the milled inner bark or wood of *Quillaja saponaria* Molina, or other *Quillaja* species, trees of the Quillajaceae family. The extract consists of a number of triterpenoid saponins consisting of glycosides of quillaic acid. Sugars—including glucose, galactose, arabinose, xylose, and rhamnose—are also present, along with tannin, calcium oxalate and other minor components. The Scientific Committee for Food (SCF) assessed the information on the safety in use of *Quillaja* extract (E 999) as food additive (emulsifier, foaming agent).

In some embodiments, the binder is selected from the group consisting of modified food starch, maltodextrin, cyclodextrin, gum arabic, inulin, and combinations thereof. In some embodiments, the binder is modified food starch. It is to be understood that any polyphenolic matrix, including suitable polyphenolic extract, emulsifiers and binders known in the art is contemplated.

Without being bound to theory, the objective of the polyphenol mediated encapsulation is to protect the bioactive molecules (vitamins and minerals) thereby contributing to an increased shelf life of the product, and promoting a controlled liberation of the molecule, increasing the bioavailability etc. Absorption of an active compound relies on the passage through membranes to reach the bloodstream. As such, when the active compound is protected and complexed within a polyphenolic matrix, the stability of the active compound inside the gastric juice is substantially increased. An improved rate and efficiency of absorption translates to higher bioavailability. As such, the compositions of the application advantageously provide higher stability of vitamins and minerals formulations and higher bioavailability of the vitamins and minerals. Moreover, the compositions of the application allow for releasing the active compound from the polyphenolic matrix at regular interval of time, or at a delayed time, and can thus provide extended or sustained release, or targeted release of vitamins and minerals. Due to this complexation of vitamins and minerals with the polyphenolic matrix with weak bonds of attraction, the vitamins and minerals are released to the active site, in a slow and controlled manner or at a particular time and/or target site. In other words, the vitamins and minerals are encapsulated within the polyphenolic matrix to provide a controlled delivery.

The compositions of the application may be formulated to provide various dosages, as known in the art and in accordance with local regulations. The dosage form, for example as a soft or hard gelatin capsule, a powder, a tablet, a syrup, or an oral strip, may also be of different sizes. Formulating specific dosage forms including the compositions of the present application is within the purview of a skilled person.

In some embodiments, the compositions of the application are formulated in a ratio of from about 1:0.1 to about: 1:1.5 of vitamin/mineral:polyphenolic matrix, expressed in w/w.

In some embodiments, the compositions of the application are formulated in a ratio of from about 1:0.1:0.01:2 to about: 1:1:0.04:8 of vitamin/mineral:polyphenolic extract: emulsifier:binder, expressed in w/w.

In some embodiments, the compositions of the application are administered to a subject by oral administration, but may be administered through inhalation, parenteral, buccal, sublingual, nasal, rectal, vaginal, patch, pump, topical or transdermal administration and the pharmaceutical compositions formulated accordingly. In some embodiments, administration is for periodic or continuous delivery. Conventional procedures and ingredients for the selection and preparation of suitable compositions are described, for example, in Remington's Pharmaceutical Sciences (2000-20th edition) and in The United States Pharmacopeia: The National Formulary (USP 24 NF19) published in 1999.

III. Methods and Uses of the Application

Vitamin and/or mineral deficiency is a common disorder; the compositions of the application may thus be useful for treating or preventing such deficiencies. Accordingly, the present application includes a composition of the application for use as a vitamin and/or mineral supplement.

The present application further provides methods for preventing or treating vitamin or mineral deficiency, comprising administering a therapeutically effective amount of a composition of the present application to a subject in need thereof.

In an embodiment, effective amounts vary according to factors such as the disease state, age, sex and/or weight of the subject. In a further embodiment, the amount of a given composition that will correspond to an effective amount will vary depending upon factors, such as the given compound (s), the pharmaceutical formulation, the route of administration, the type of condition, disease or disorder, the identity of the subject being treated, and the like, but can nevertheless be routinely determined by one skilled in the art.

In some embodiments, the subject is a mammal. In some embodiments, the subject is human.

IV. Methods of Preparing the Compositions of the Application

Compositions of the present application can be prepared by various processes. The selection of a particular process to prepare a given composition is within the purview of the person of skill in the art.

In some embodiments, the compositions are prepared by mixing said at least one vitamin and mineral, and said polyphenolic matrix; homogenizing the mixture to allow encapsulation of at least one vitamin and mineral in the polyphenolic matrix and homogenizing the mixture thereby forming the polyphenolic matrix around the vitamin and/or mineral.

In some embodiments, the method further comprises formulating the composition into an acceptable pharmaceutical form. A skilled person in the art would use methods know in the art for mixing, milling, homogenizing and formulating the compositions into the desired final formulations. In one embodiment, the compositions are prepared and formulated as a soft gelatin capsule for oral administration.

In some embodiments, the compositions are prepared in the form of a powder. For example, the vitamins and/or minerals are complexed and protected within the polyphenolic matrix components, and may be spray dried to provide a powder formulation. Spray drying may be performed according to known methods. In some embodiments, the mixture is spray dried using cellulose. The powder formulation may then be used to form tablets, suspensions, etc.

EXAMPLES

The following non-limiting examples are illustrative of the present application.

General Methods

The starting materials used for the below formulations are commercially available, and were thus obtained from various commercial sources.

Example 1—Vitamin C Formulation

This Example is directed to a concentration of vitamin C of 350 mg/dose, wherein the single oral dose is standardized to 750 mg in a hard gelatin capsule. The components include:
1. 350 mg—Ascorbic acid (vitamin C)
2. 60-80 mg of pomegranate peel extract (specific extract having 30-40% total polyphenols content)
3. 10-15 mg *Quillaja saponaria* extract
4. 240-280 mg sodium octenylsuccinate starch
5. 150 mg cellulose (for preparation of capsules)

In a typical procedure, a pre-complexing mixture was prepared using 400 g of sodium ocenylsuccinate dissolved in 6 L of water. This mixture was warmed to 60-70° C. To this warm solution, 100 g of pre-extracted pomegranate extract was added with constant stirring. After the addition of the pomegranate extract, the solution was again stirred for 2 hours at 60° C. After the complete dispersion of pomegranate extract into the starch solution, 5.5 g of *Quillaja extract* along with 550 g of vitamin C pre-dissolved in 2 L of water was carefully added to the pomegranate—starch mixture. After the addition of vitamin C, the entire system was stirred for an hour, then subjected to high pressure homogenization. After the homogenization, the solution was spray dried to get a fine powder. The collected powder kept under nitrogen to avoid any oxidation. This powder was again mixed with 200 g of cellulose under nitrogen to increase the flowability before capsulation.

While the applicant's teachings described herein are in conjunction with various embodiments for illustrative purposes, it is not intended that the applicant's teachings be limited to such embodiments as the embodiments described herein are intended to be examples. On the contrary, the applicant's teachings described and illustrated herein encompass various alternatives, modifications, and equivalents, without departing from the embodiments described herein.

I claim:

1. A composition comprising at least one vitamin and mineral in a polyphenolic matrix comprising a mixture of at least one polyphenolic extract, at least one emulsifier and at least one binder, wherein the composition has a ratio of from about 1:0.1:0.01:2 to about: 1:1:0.04:8 of vitamin/mineral:polyphenolic extract:emulsifier:binder, expressed in w/w.

2. The composition of claim 1, wherein said polyphenolic extract is selected from the group consisting of a fruit peel extract, gallic acid, ellagic acid, punicalagin, catechin, chlorogenic acid, epicatechin and combinations thereof.

3. The composition of claim 2, wherein said fruit peel extract is selected from the group consisting of pomegranate peel extract, banana peel extract, amla peel extract, orange peel extract, mango peel extract, melon peel extract, water melon peel extract, tea extract and combinations thereof.

4. The composition of claim 1, wherein said at least one emulsifier is selected from the group consisting of *Quillaja saponaria* extract, locust bean gum, gum arabic, cellulose gum, xanthan gum and combinations thereof.

5. The composition of claim 1, wherein said at least one binder is selected from the group consisting of modified food starch, maltodextrin, cyclodextrin, gum arabic, inulin, and combinations thereof.

6. A composition comprising at least one vitamin and mineral in a polyphenolic matrix comprising a mixture of at least one fruit peel extract, at least one emulsifier and at least one binder, wherein the composition has a ratio of from about 1:0.1:0.01:2 to about: 1:1:0.04:8 of vitamin/mineral:fruit peel extract:emulsifier:binder, expressed in w/w.

7. The composition of claim 6, wherein said fruit peel extract is selected from the group consisting of pomegranate peel extract, banana peel extract, amla peel extract, orange peel extract, mango peel extract, melon peel extract, water melon peel extract, tea extract and combinations thereof.

8. The composition of claim 6, wherein said at least one emulsifier is selected from the group consisting of *Quillaja saponaria* extract, locust bean gum, gum arabic, cellulose gum, xanthan gum and combinations thereof.

9. The composition of claim 6, wherein said at least one binder is selected from the group consisting of modified food starch, maltodextrin, cyclodextrin, gum arabic, inulin, and combinations thereof.

10. A composition comprising at least one vitamin and mineral in a polyphenolic matrix comprising a mixture of at least one pomegranate peel extract, at least one *Quillaja saponaria* extract and at least one modified food starch, wherein the composition has a ratio of from about 1:0.1:0.01:2 to about: 1:1:0.04:8 of vitamin/mineral:pomegranate peel extract:*Quillaja saponaria* extract:modified food starch, expressed in w/w.

11. The composition of claim 10, wherein the pomegranate peel extract has a polyphenols content from 30-40% w/w of the total weight of extract.

12. The composition of claim 1, wherein the composition is for oral administration.

13. The composition of claim 1, wherein the composition is formulated in the form of a capsule, a powder, a tablet, a syrup or an oral strip.

14. The composition of claim 1, wherein the composition is formulated for extended release.

15. The composition of claim 6, wherein the composition is for oral administration.

16. The composition of claim 6, wherein the composition is formulated in the form of a capsule, a powder, a tablet, a syrup or an oral strip.

17. The composition of claim 6, wherein the composition is formulated for extended release.

18. The composition of claim 10, wherein the composition is for oral administration.

19. The composition of claim 10, wherein the composition is formulated in the form of a capsule, a powder, a tablet, a syrup or an oral strip.

20. The composition of claim 10, wherein the composition is formulated for extended release.

* * * * *

UNITED STATES PATENT AND TRADEMARK OFFICE
CERTIFICATE OF CORRECTION

| | | |
|---|---|---|
| PATENT NO. | : 11,890,345 B2 | Page 1 of 1 |
| APPLICATION NO. | : 17/517197 | |
| DATED | : February 6, 2024 | |
| INVENTOR(S) | : Fabrizio Di Stefano | |

It is certified that error appears in the above-identified patent and that said Letters Patent is hereby corrected as shown below:

On the Title Page

Item (73) Assignee:
"ProMedXInnovations Inc., Thornhill (CA)"
Should read:
-- ProMedX Innovations Inc., Thornhill (CA) --

Signed and Sealed this
Ninth Day of July, 2024

Katherine Kelly Vidal
*Director of the United States Patent and Trademark Office*